United States Patent [19]

Scott

[11] Patent Number: 5,708,031

[45] Date of Patent: *Jan. 13, 1998

[54] PROSTAGLANDIN E2 TREATMENT OF IMPOTENCE

[76] Inventor: Nathan E. Scott, 301 W. Bastanchury, Suite 15, Fullerton, Calif. 92835

[*] Notice: The terminal 29 months of this patent has been disclaimed.

[21] Appl. No.: 90,483

[22] Filed: Jul. 12, 1993

Related U.S. Application Data

[63] Continuation of Ser. No. 860,107, Mar. 30, 1992, abandoned, which is a continuation of Ser. No. 725,350, Jul. 3, 1991, abandoned.

[51] Int. Cl.$^6$ .................................................. A61K 31/557
[52] U.S. Cl. .................................................. 514/573
[58] Field of Search ............................... 514/560, 573

[56] References Cited

U.S. PATENT DOCUMENTS

| | | | |
|---|---|---|---|
| 4,311,707 | 1/1982 | Birnbaum et al. | 514/573 |
| 4,801,587 | 1/1989 | Voss et al. | 514/248 |
| 4,955,878 | 9/1990 | See et al. | 514/573 |

FOREIGN PATENT DOCUMENTS 9002545  3/1990  WIPO.

OTHER PUBLICATIONS

Schramek et al, Derwent Drug File Abstracts, vol. 90, abstract No. 01345, 1989.

"Impotence," *Medical Aspects of Human Sexuality*, pp. 66–68, May 1991.

Gauger, Laura J. and Curet, Louis B., "Comparative Efficacy of Intravaginal Prostaglandin E-2 in the Gel and Suppository Forms for Cervical Ripening,"*DICP, The Annals of Pharmacotherapy*,25:456–460,May 91.

Cavallini, Giorgio, "Minoxidil vs. Nitroglycerine: A Perspective Double Blind Controlled Trial in Transcutaneous Erection Facilitation for Organic Impotence,"*The Journal of Urology*, 146:50–53. Jul. 1991.

Artoux, Michelle J., "Alprostadil in Impotence,"*DICP, The Annals of Pharmacotherapy*, 25:363–365, Apr. 1991.

Burnakis, Thomas G., "Amyl Nitrite for the Treatment of Penile Tumescence," *Hospital Pharmacy*, 26:343–344, Apr. 1991.

*Physicians' Desk Reference*, 45th ed., pp. 627–628, 1991.

Lehninger, Albert L., *Biochemistry*, 2nd ed., 1975.

Ganong, William F., *Review of Medical Physiology*, 7th ed., pp. 187, 226, 1975.

*Physicians' Desk Reference*, 45th ed., pp. 2250–2251, 1991.

Catanzarite, Valerian A. and Aisenbrey, Gary, "Prostaglandins: Mundane and Visionary Applications," *Contemporary OB/Gyn*, pp. 21–41, Oct. 1987.

"Agents for Patent Ductus Arteriosus," *Facts & Comparisons*, pp. 732–732a, Nov. 1989.

"Prostin E-2," package insert of the Upjohn Company, revised Oct. 1990.

"Hemabat," package insert of the Upjohn Company, Nov. 1989.

*Primary Examiner*—William R. A. Jarvis
*Attorney, Agent, or Firm*—Michael J. Ram; Marvin H. Kleinberg; Marshall A. Lerner

[57] ABSTRACT

Disclosed are compositions and methods for the treatment of male impotence, wherein erectile dysfunction is alleviated by administering a pharmaceutically acceptable formulation containing prostaglandin $PGE_2$. An antidote for the effects of administration of the $PGE_2$, or for treating priapism of other etiology, is also disclosed.

19 Claims, No Drawings

PROSTAGLANDIN E2 TREATMENT OF IMPOTENCE

This application is a continuation of application Ser. No. 07/860,107, filed Mar. 30, 1992, now abandoned, which is a continuation of Ser. No. 07/725,350, filed Jul. 3, 1991, now abandoned.

BACKGROUND OF THE INVENTION

The present invention relates to the treatment of impotence, and, more particularly, to the reversible pharmaceutical treatment of impotence using prostaglandin $PGE_2$.

In excess of about 10 million men in the United States alone exhibit sufficient erectile dysfunction that they can be characterized as effectively impotent. Impotence in the human male can arise from a variety of psychological and physiological etiologies. For example, long term diabetes, damage to the spinal cord, multiple sclerosis, or nerve damage resulting for example from lower abdomen or prostate surgery, and advancing age can result in impotence. For differing reasons, each of the foregoing result in an inability to pressurize the corpora cavernosa, which can result in turn from either an insufficient arterial inflow on the supply side, or an insufficient increase in the venous output resistance to blood flow.

A wide variety of mechanical means have been provided, in an effort to overcome erectile dysfunction. For example, U.S. Pat. No. 4,596,242 to Fischell discloses a surgically implantable hydraulic system, having a fluid reservoir and pressure generator, a patient manipulable valve, a pressure reservoir and a distensible member responsive to actuation of the valve. A variety of other prior art mechanical implants and other devices for this purpose are described in the Background of the Invention section of U.S. Pat. No. 4,596,242.

In addition to the mechanical efforts to overcome erectile dysfunction, pharmaceutical approaches have been tried as well. For example, prostaglandin E1 has been observed to produce erection in some cases, but only by direct percutaneous injection into the penis.

Notwithstanding the foregoing, there remains a need for an improved treatment of erectile dysfunction. Surgical implantation and/or repeated injections range from disfavored to medically disadvantageous, and do not, as a whole, provide a satisfactory solution to the problem. From a patient usability standpoint, erectile dysfunction would most advantageously be treated on a self-administration basis, without the need for surgical intervention or repeated injections of a pharmaceutical agent.

SUMMARY OF THE INVENTION

In accordance with one aspect of the present invention, there is provided a method of treating erectile dysfunction in a male patient, comprising the step of administering to the patient a unit dose of a formulation comprising an erectile dysfunction treating amount of a prostaglandin E2 compound, or pharmaceutically acceptable salts or derivatives thereof. The prostaglandin E2 compound is preferably formulated together with a pharmaceutically acceptable delivery medium, which may comprise local anesthetic agents and/or a lubricant. Preferably, the anesthetic agent comprises lidocaine.

A unit dose of the formulation in accordance with the present invention will typically be less than about 5 cc in volume, preferably less than about 3 cc and most preferably within the range of from about 1 cc to 2 cc. The amount of active ingredient in a unit dose will typically be within the range of from about 0.2 mg to about 5.0 mg. More preferably, the amount of prostaglandin E2 in a unit dose will be within the range of from about 0.6 mg to about 1.8 mg in a formulation not also including lidocaine, and from about 1.2 mg to about 3.6 mg in a formulation including lidocaine.

The administration step of the method in accordance with the present invention comprises the transurethral administration of the unit dose of formulation. In an embodiment where the formulation comprises a cream or gel form, the formulation is preferably transurethrally instilled or inserted such as by extrusion through a syringe or unit dose administration packet comprising an elongate tubular administration tip.

In an embodiment of the present invention, wherein the administrable form of the formulation comprises a relatively rigid suppository, the suppository can be manually inserted into the distal opening of the urethra.

In accordance with a further aspect of the present invention, there has been provided a formulation and method for relieving the erectile dysfunction treating effects of the application of a formulation comprising prostaglandin E2, or of treating priapism of other etiology. In accordance with this antidote method, an effective antidotal amount of a formulation comprising a 15 methyl substituted prostaglandin F2α or pharmaceutically acceptable salt is administered in the same manner as described above.

These and further objects and advantages of the present invention will become apparent from the Detailed Description of Preferred Embodiments which follows, considered together with the appended claims.

DETAILED DESCRIPTION OF PREFERRED EMBODIMENTS

The prostaglandins are a series of cyclic derivatives of certain unsaturated fatty acids. They are found in a variety of tissues, including the prostate gland, the seminal vesicles, the lungs and the brain. These naturally occurring prostaglandins are derived by cyclization of 20-carbon unsaturated fatty acids such as arachidonic acid. See Lehninger, Albert L., *Biochemistry*, 2d ed. (1975), p. 300 (hereinafter "Lehninger").

Carbon atoms of the fatty acid backbone are cyclized to form a characteristic 5-membered ring. The prostaglandins are divided into a number of groups, including those designated A–F, based on the configuration of the ring structure. Prostaglandins also differ in stereochemistry and in the number of side chain double bonds which are conventionally indicated by a subscript number. Thus, for example, prostaglandin $E_2$ ("PGE2") has the ring configuration characteristic of the E group and contains two side chain double bonds. The chemical name for $PGE_2$ is (5Z,11α,13E,15S)-11,15-Dihydroxy-9-oxo-prosta-5,13-dien-1-oic acid and the structural formula of one form is represented in Formula I, below. The molecular formula is $C_{20}H_{32}O_5$.

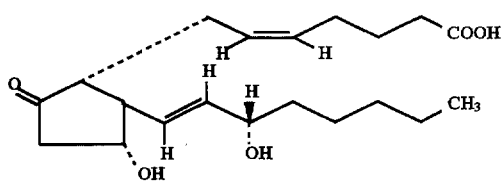

The biosynthesis of prostaglandins has been well characterized. See, e.g., Lehninger at p. 687. In a typical biosynthetic pathway, exemplified by production of $PGE_2$, the essential fatty acid linoleic acid is converted into the 20-carbon arachidonic acid, which is then acted upon by prostaglandin synthase, a dioxygenase enzyme. Oxygen atoms are added at carbon atoms 9 and 15, and the product is cyclized by formation of a bond between carbon atoms 8 and 12. In the presence of reduced glutathione, this cyclized product undergoes conversion into prostaglandin $PGE_2$. Other types of naturally occurring prostaglandins are derived from different polyunsaturated fatty acids.

In about the 1960s, prostaglandins were isolated from a particular species of Caribbean coral, which made them more widely available for research. Catanzarite, Valerian A. and Gary Aisenbrey, *Contemporary OB/GYN* (October 1987), p. 22 (hereinafter "Catanzarite"). A large number of natural and synthetic analogues of the prostaglandins are now known. Lehninger at 687.

The prostaglandins are known to produce often unpredictable effects over a very wide range of biological activities of a hormonal or regulatory nature. Prostaglandins have been reported to both lower and raise blood pressure, to inhibit gastric secretion, dilate bronchi, inhibit lipolysis, antagonize vasopressin-induced anti-diarrhesis, constrict the pupil, increase and decrease the intraocular pressure and produce contraction of the uterus. See, e.g., Ganong, William F., *Review of Medical Physiology*, 7th ed. (1975), p. 226 (hereinafter "Ganong"). The naturally occurring prostaglandins all appear to be capable of affecting the control of vascular and other smooth muscle contractions. In the central nervous system, prostaglandins are known to modify responses to certain synaptic transmitters. They have been reported to mimic the actions of some hormones and to inhibit the actions of certain others. See Ganong at 226.

Two of the most extensively studied of the prostaglandins are $PGE_2$ and $PGF_{2\alpha}$. Both of these molecules are synthesized within the pregnant and non-pregnant uterus. While $PGE_2$ and $PGF_{2\alpha}$ are similar in mediating some effects, they are different with respect to certain others. Both cause uterine contractions, but they predominate at different sites within the uterus—$PGE_2$ in the lower uterine segment, $PGF_{2\alpha}$ in the fundal region. Both play important roles during labor, but $PGE_2$ has its major effect in cervical ripening, whereas $PGF_{2\alpha}$ is more important in generating uterine contractions. $PGE_2$ elevates body temperature, whereas $PGF_{2\alpha}$ has no apparent effect on body temperature. $PGE_2$ is vasodilator and bronchodilator, while $PGF_{2\alpha}$ is a bronchoconstrictor and vasoconstrictor. See Catanzarite at 21–22.

Prostaglandins have been used in gynecology for pregnancy termination. Preparing the cervix with a prostaglandin suppository has been found to reduce the incidence of cervical laceration and significant bleeding. See Catanzarite at page 22. Synthetic analogues of prostaglandin $PGE_2$, such as 16-16-dimethyl $PGE_2$ and 9-methylene $PGE_2$, have proven useful for the induction of first trimester abortions. Such procedures typically use vaginal suppositories containing 20 milligrams $PGE_2$ or 3 milligrams of 15-methyl $PGF_{2\alpha}$, or by repeated intramyometrial injections of 15-methyl $PGF_{2\alpha}$, or by infusing a $PGF_{2\alpha}$-urea mixture (20 milligrams of $PGF_{2\alpha}$ and 40 milligrams of urea in 100 mL of 5% dextrose in water) into the amniotic sac.

In obstetrics, prostaglandins have been used for cervical ripening, labor induction and control of post-partum hemorrhage. Catanzarite at 29. For cervical ripening, $PGE_2$ has been given intravenously, orally and vaginally, but the preferred route is intracervically. A $PGE_2$ gel is now commercially available in Scandinavia, and another $PGE_2$ gel is being investigated in the United States. The $PGE_2$ gel can also be used for labor induction (3–5 mg of $PGE_2$, prepared by blending a 20 mg suppository with 60 mL of lubricating jelly and using 9–15 mL of the mixture, is placed in the vagina). Catanzarite at 32. Prostaglandins have also been utilized to control post-partum hemorrhage.

Since circulating prostaglandins can be rapidly metabolized in the lungs, liver and kidneys, a number of synthetically modified prostaglandins have been developed that are not metabolized as quickly. See, e.g., Catanzarite at 32.

Prostaglandin $PGE_2$, also known as the "Prostin E2" brand of "dynoprostone," is available from the Upjohn Company in the form of a vaginal suppository. Indications and usage reported by Upjohn are (i) termination of pregnancy from the 12th through the 20th gestational week, (ii) evacuation of the uterine contents in the management of missed abortion or intrauterine fetal death up to 28 weeks of gestational age, and (iii) in the management of non-metastatic gestational trophoblastic disease (benign hydatidiform mole). See The Upjohn Co., Prostin E2 product description 810 994 009, Oct., 1990.

Contraindications to the use of prostaglandin $PGE_2$ include hypersensitivity to dynoprostone, acute pelvic inflammatory disease, or patients with active cardiac pulmonary renal or hepatic disease. Upjohn notes that although carcinogenic bioassay studies have not been conducted in animals for $PGE_2$ (because of the limited indications for use and the short duration of administration), there was no evidence of mutagenicity in either the Micronucleus Test or in the Ames Assay. Upjohn also indicates that a number of adverse reactions may be observed with the use of $PGE_2$ for abortions. These adverse reactions are related to $PGE_2$'s contractile effect on smooth muscle and include vomiting, temperature elevations, diarrhea, nausea, transient diastolic blood pressure decreases, and a number of other effects. Upjohn's vaginal suppository contains 20 mg of $PGE_2$ in a mixture of glycerides of fatty acids.

Upjohn markets an (15S)-15-methyl analogue of prostaglandin $PGF_{2\alpha}$ under the brand name Hemabate®, and also known as "carboprost tromethamine sterile solution." The structural formula of Hemabate® is represented in Formula II below:

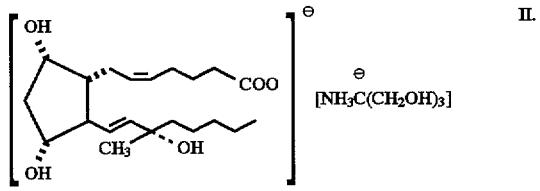

Upjohn reports that Hemabate® is indicated for aborting pregnancy between the 13th and 20th weeks of gestation, in certain conditions related to second trimester abortions, and in the treatment of post-partum hemorrhage. See The Upjohn Co., product description 814 350 002, Nov., 1989. For abortion, the prostaglandin solution is injected using a syringe and administered deep in the muscle. Intramuscular injection is also used for treating post-partum uterine bleeding.

Upjohn also markets prostaglandin PGE1, as the "Prostin VR Pediatric" brand of "alprostadil sterile solution," which is used to temporarily maintain the patency of the ductus arteriosus until corrective surgery can be performed in neonates having congenital heart defects and who depend upon the patent ductus for their survival. For the administration of $PGE_1$ in neonates, Upjohn recommends continuous intravenous infusion into a large vein, or administration through an umbilical artery catheter placed at the ductal opening. See The Upjohn Co., product description 811 987 004, in Physician's Desk Reference, 45th Edition, p.2250 (1991).

Quite surprisingly, the inventor herein has discovered that transurethral application of $PGE_2$ can in many cases provide an effective, reversible treatment of erectile dysfunction in human males. Thus, in accordance with one embodiment of the present invention, $PGE_2$ or a pharmaceutically acceptable salt, ester or other derivative thereof is formulated together with a carrier medium which may comprise any of a variety of additional excipients or adjuvants into a form suitable for transurethral delivery. In accordance with another aspect of the present invention, there is provided an antidote for reversing the effects of the foregoing $PGE_2$ treatment, comprising administration of an antidotal amount of a $PGF_{2\alpha}$, or pharmaceutically acceptable salts, esters or derivatives thereof. Preferably, 15-methyl $PGF_{2\alpha}$ is utilized for this purpose.

Preferably, the $PGE_2$ or $PGF_{2\alpha}$ formulation will comprise a cream or gel, although a more solid form such as pellets or a rod-shaped suppository body may also be used. Although low viscosity gels or liquids may also be formulated, the liquid form may present handling and delivery difficulties and may not present a sufficient dwell time in the urethra to permit absorption of an efficacious amount of the active ingredient.

Administration of the cream or gel form may be accomplished by transurethral delivery using a syringe without a needle, or with a short blunt cannula attached. The gel or cream forms are preferably provided in unit dose amounts for self administration by the patient. For this purpose, compressible unit does packages are preferably provided with an elongate tubular delivery spout, sized for transurethral insertion. Following transurethral installation of any of the liquid, gel or cream forms, the distal end of the urethra is preferably occluded, such as by manual pressure for up to several minutes, to permit sufficient dwell time for absorption.

Typically, a lubricant and/or a local anesthetic for desensitization will also be provided for use as needed. In one embodiment, the $PGE_2$, lubricant and anesthetic are all formulated into a convenient cream. This cream may be prepared, for example, by mixing one Upjohn Prostin E2® $PGE_2$ suppository together with 10 cc of a lidocaine jelly such as Xylocaine® 2% jelly (available from Astra Pharmaceutical Products) and 50 cc. of a surgical lubricant such as K-Y jelly (available from Johnson & Johnson). Lidocaine HCl, available in a variety of formulations, comprises acetamide, 2-(diethylamino)-N-(2,6-dimethylphenyl)-monohydrochloride.

The amount of lubricant and the amount and concentration of anesthetic can be varied considerably as will be apparent to one of skill in the art. For example, lidocaine jelly can be used having anywhere from about 1% to about 10% and preferably about 2% lidocaine. Percentages much lower than about 1% are less desirable due to the requirement of a relatively large volume of jelly to deliver an effective dose of lidocaine. In general, the anesthetic level can largely be dictated by patient preference, as determined through routine experimentation. Although the incidence of adverse effects with Xylocaine® 2% jelly is very low, caution should be exercised when applying large amounts since the frequency of adverse effects is directly proportional to the total dosage of the local anaesthetic administered. See Astra Pharmaceuticals, product description 021838R11, June 1986; in Physician's Desk Reference, 45th Edition (1991), at p. 628.

A variety of other anesthetic agents can also be used with the formulation of the present invention, as will be appreciated by one of skill in the art. For example, novocaine, procaine, tetracaine or benzocaine may be selected. Patients allergic to para-aminobenzoic acid derivatives such as procaine, tetracaine and benzocaine have not appeared to show cross sensitivity to lidocaine. Lidocaine is also contraindicated in patients with a history of sensitivity to amide type local anesthetics. Xylocaine® 2% jelly also contains methylparaben, propylparaben and hydroxypropylmethylcellulose, as well as lidocaine; and, therefore, Xylocaine® is contraindicated for patients with known sensitivities to any of these compounds. See Astra Pharmaceuticals, product description 021838R11, June 1986; in Physician's Desk Reference, 45th Edition (1991), at p. 628.

It has been determined by the inventor that the effect of the $PGE_2$ treatment is generally less pronounced when delivered in a formulation which also comprises lidocaine. Thus, in a lidocaine-containing formulation, the dosage of $PGE_2$ is preferably increased over that in a non-lidocaine-containing formulation, and more preferably, the $PGE_2$ dosage is preferably doubled in a lidocaine-containing formulation.

More or less lubricant may be desired depending upon the delivery dose and concentration of the anesthetic Jelly. In general, the total volume of the impotence treating unit dose should be no more than about 5 cc, and preferably from about 1 cc to no more than about 2 cc due to the inherent capacity of the urethra. Doses of excessive volume can result in painful administration, and also in retrograde migration of the excess formulation into the prostatic urethra or bladder.

Preferably, the total amount of $PGE_2$ contained in a unit dose will be within the range of from about 0.2 mg to about 5.0 mg. Due to differing etiology of erectile dysfunction, and inherent variations across a population in terms of responsiveness to pharmaceutical agents, some routine experimentation may be desired to determine optimum dosages for a given patient or class of patients.

In general, however, doses within the range of from about 0.5 to about 5.0, and preferably from about 0.6 to about 3.6 mg $PGE_2$, have generally proven sufficient in patients in which a response is likely to occur. Although it is not possible to predict with precision what types of patient populations will likely respond to the treatments disclosed herein, certain classes of patients are anticipated to be treatable depending upon the etiology of the condition. For example, patients in whom erectile dysfunction is associated with vascular abnormalities such as atherosclerosis which prevents adequate blood inflow are not likely to respond. Patients in whom the dysfunction is a result of such conditions as diabetes, denervation, or psychological status are expected to be more likely to respond.

In the antidotal or priapism treating PGF formulation, the PGF will generally be present in an amount within the range of from about 5 to about 50 µg per 1 cc dose of formulation, preferably within the range of from about 8 to 20 µg/cc and more preferably about 12 µg/cc. As with the PGE formulation, optimum dosage for a given patient can be determined through routine experimentation.

Any of several different delivery systems may be utilized in accordance with the method of the present invention. For example, if a fluid or cream or gel system is used, the carrier can be absorbed directly, or allowed to be expelled following sufficient dwell time which may be controlled by occluding the distal end of the urethra.

Alternatively, more solid delivery vehicles may be used such as an ovoid or rod-shaped suppository. Suppositories can be formulated from any of a variety of materials which exhibit sufficient physical integrity to permit transurethral insertion and which will then permit delivery of the medication. Once installed, the structural component of the suppository may break down under the influence of body heat. Alternatively, materials can be used which will dissolve in an aqueous environment at a pH within the range of that typical of the urethra. One suitable composition is a mixture of glycerides of fatty acids such as that used with the Prostin E2® product.

As a further alternative, a variety of drug delivery vehicles may be used which neither dissolve nor break down in the environment of the urethra. Relatively rigid rod-shaped delivery vehicles may be fashioned from materials having a microporous structure for the time release of entrapped pharmaceutical.

Such vehicles can be transurethrally inserted for a predetermined period of time and then removed following delivery of an efficacious amount of drug. Although the convenience of a self dissipating carrier is lost, the removable time release delivery structure may have the added advantage of providing some range of flexibility in the total delivered dose. Thus, the patient, by leaving the implant in place for relatively shorter or longer periods of time, can optimize the dose within a preset maximum range.

Particular embodiments of the present invention will be described in the Examples which follow.

EXAMPLE I

Preparation of Intraurethral $PGE_2$ Cream

A batch of $PGE_2$ cream was prepared by mixing a 40 mg $PGE_2$ suppository (obtained as the "Prostin E2" suppository from the Upjohn Company) with 10 cc of 2% xylocaine jelly and 50 cc of K-Y surgical lubrication jelly (hydroxyethylcellulose, obtained from Johnson & Johnson). Mixing was accomplished by stirring until the mixture appeared homogenous upon visual inspection. The result was a $PGE_2$ cream having approximately 1.3 mg of $PGE_2$ per 2 cc of cream.

EXAMPLE II

Preparation of Intraurethral $PGE_2$ Gel

The homogenicity of a batch of $PGE_2$ is ensured by inclusion of a methylene blue marker. One 20 mg $PGE_2$ suppository ("Prostin E2" from the Upjohn Company) is sliced into thin slices and allowed to soften at room temperature for 15 minutes. A small drop of 1% methylene blue solution (American quinine, Shirley, N.Y.) is placed onto each slice to serve as a marker for homogenicity. The softened slices are thereafter geometrically mixed with the contents of a 56.7 gram tube of K-Y jelly to yield a homogenous mixture, as evidenced by blue color uniformity. The theoretical content of the final product is approximately 0.67 milligrams of $PGE_2$ per 2 cc of gel.

EXAMPLE III

Preparation of Lipid Based Intraurethral $PGE_2$ Cream

A batch of $PGE_2$ cream in cocoa butter is prepared by placing one 20 mg. $PGE_2$ suppository (Prostin E2 by the Upjohn Company) into a porcelain evaporating dish and is melted in a 37° C. water bath. Shredded cocoa butter is added to the melted suppository with stirring to bring the total mass to approximately 20 grams. As the melting continues, the temperature of the mixture is kept at or below about 33° C. Higher temperatures are to be avoided, as they have been reported to cause the crystalline form of the cocoa butter to change, resulting in aberrations in bioavailability. Transformations in the crystalline form of the cocoa butter are visually observed as a change from opalescent to transparent. After complete melting, the mixture is stirred thoroughly and poured into suppository molds. The material is thereafter allowed to cool at room temperature for about 15 minutes, and thereafter is placed in the refrigerator to facilitate further solidification. The suppositories may thereafter be removed from the mold, individually packaged and placed in refrigerated storage under anhydrous conditions.

EXAMPLE IV

Administration of Intraurethral $PGE_2$ Cream

Two cc of the $PGE_2$ cream from Example 1 was instilled into the urethral meatus of each of 10 impotent male patients between the ages of 50 and 70, using a syringe. The cream was massaged down the urethra, and then the distal end of the urethra was occluded for 5 minutes by manual pressure.

EXAMPLE V

Efficacy of $PGE_2$ Cream in Treating Human Erectile Dysfunction

The effect of administration of $PGE_2$ cream, prepared and administered in accordance with the procedures of Examples I and IV, was observed. After 15 to 30 minutes, treatment response was rated as no penile tumescence, partial tumescence or full tumescence.

As a result, two of the ten men treated had no response, six had partial tumescence, and two had full tumescence. Thus, 80% of the men treated showed at least partial penile tumescence in response to the intraurethral $PGE_2$ cream.

EXAMPLE VI

Efficacy of Lower Concentrations of $PGE_2$ Cream in Treating Human Erectile Dysfunction $PGE_2$ cream was prepared and administered in accordance with the procedures of Examples I and IV, except that a 20 mg $PGE_2$ suppository was used instead of a 40 mg suppository. This cream contained approximately 0.7 mg of $PGE_2$ per 2 cc of cream. Two cc of cream was used to treat each of ten impotent men between the ages of 50 and 70. After 15 to 30 minutes, treatment response was rated as no penile tumescence, partial tumescence, or full tumescence.

As a result, four of the ten men treated had no response, two had partial tumescence, and four had full tumescence.

Thus, even using lower concentrations of PGE$_2$, 60% of the men treated showed at least partial penile tumescence in response to the intraurethral PGE$_2$ cream.

EXAMPLE VII

Use of PGF$_{2\alpha}$ to Counteract Effects of Administration of PGE$_2$

Priapism resulting from the PGE$_2$ treatment in accordance with the present invention has been determined to be reversible or treatable through the application of an effective antidotal amount of a 15 methyl substituted prostaglandin F2α containing formulation. In addition, it is anticipated that priapism of a variety of other etiology will be similarly treatable.

An antidotal formulation is prepared by mixing approximately 250 micrograms of prostaglandin F2α obtained as Hemabate, marketed by Upjohn, in approximately 20 cc of K-Y jelly. Mixing is accomplished manually until visual observation reveals a homogenous composition. A dose of approximately 1 cc of the foregoing formulation is instilled in accordance with Example IV, to reverse the results of the PGE$_2$ treatment in accordance with the present invention.

Although this invention has been described in terms of certain preferred embodiments, other embodiments that are apparent to those of ordinary skill in the art are also within the scope of the invention. In particular, analogs or derivatives of PGE$_2$ and PGF$_{2\alpha}$ which do not affect the basic functionality of those molecules as described herein are also considered within the scope of the present invention. Accordingly, the scope of the invention is intended to be defined only by reference to the appended claims.

I claim:

1. A method of treating erectile dysfunction in a male patient, comprising the step of administering to the urethra of the patient a unit dose of a formulation comprising an erectile dysfunction treating amount of a compound having the structural formula:

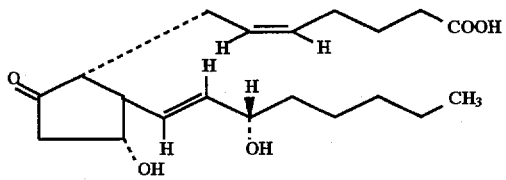

or pharmaceutically acceptable salt or ester thereof, together with a pharmaceutically acceptable delivery medium.

2. A method as in claim 1, wherein said administration step further comprises occluding the urethra distally of the formulation to prevent the escape thereof.

3. A method as in claim 1, wherein said formulation further comprises an anesthetic agent.

4. A method as in claim 3, wherein said anesthetic agent comprises lidocaine.

5. A method as in claim 1, wherein said formulation further comprises a lubricating agent.

6. A method as in claim 1, wherein said formulation is in the form of a cream or gel.

7. A method as in claim 1, wherein said formulation is in the form of a suppository.

8. An elongated drug delivery vehicle dimensioned for transurethral insertion, said delivery vehicle containing about 2 cc of a composition comprising an erectile dysfunction treating amount of prostaglandin E$_2$ or pharmaceutically acceptable salt thereof and a delivery medium for the transurethral delivery of said formulation, the amount of prostaglandin E$_2$ being less than about 5.0 mg.

9. A formulation as in claim 8, further comprising an anesthetic agent.

10. A formulation as in claim 8, further comprising a lubricant.

11. A delivery vehicle as in claim 8, wherein the structural integrity of said vehicle is provided by a material which softens under the influence of body heat.

12. A delivery vehicle as in claim 8, wherein the structural integrity of said vehicle is provided by a material which is dissolvable in an aqueous environment.

13. A delivery vehicle as in claim 8, wherein said delivery vehicle comprises a time-release drug delivery medium.

14. A method as in claim 1, wherein said unit dose comprises within the range of from about 10 mg to about 50 mg of said compound.

15. A method as in claim 1, wherein said unit dose of formulation comprises within the range of from about 0.2 mg to about 3.6 mg of said compound.

16. A method of reversing the erectile dysfunction treating effect of administration of the delivery vehicle of claim 2, comprising the step of administering to the urethra of a patient a unit dose of an antidote formulation comprising a compound having the structural formula:

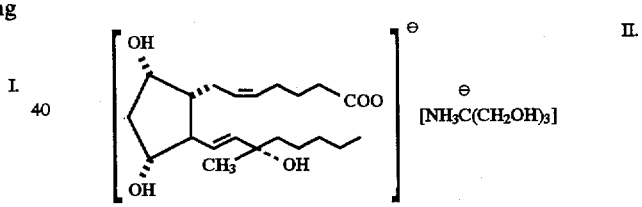

or pharmaceutically acceptable salt thereof, together with a pharmaceutically acceptable delivery medium.

17. A method as in claim 16, wherein said unit dose comprises within the range of from about 5 µg to about 50 µg of said compound.

18. A method as in claim 17, wherein said unit dose comprises from about 8 µg to about 20 µg of said compound.

19. A method as in claim 16, wherein the administering step comprises transurethrally administering said antidote formulation.

* * * * *